(12) United States Patent
Park et al.

(10) Patent No.: US 11,439,327 B2
(45) Date of Patent: Sep. 13, 2022

(54) APPARATUS AND METHOD FOR MEASURING RAMAN SPECTRUM

(71) Applicant: SAMSUNG ELECTRONICS CO., LTD., Suwon-si (KR)

(72) Inventors: Yun S Park, Suwon-si (KR); Woo Chang Lee, Anyang-si (KR); Ho Jun Chang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 363 days.

(21) Appl. No.: 16/816,489

(22) Filed: Mar. 12, 2020

(65) Prior Publication Data

US 2020/0397353 A1 Dec. 24, 2020

(30) Foreign Application Priority Data

Jun. 18, 2019 (KR) .......................... 10-2019-0072236

(51) Int. Cl.
| | |
|---|---|
| *G01J 3/44* | (2006.01) |
| *A61B 5/145* | (2006.01) |
| *G01J 3/02* | (2006.01) |
| *G01N 21/65* | (2006.01) |
| *A61B 5/1455* | (2006.01) |

(52) U.S. Cl.
CPC ........ *A61B 5/14532* (2013.01); *A61B 5/1455* (2013.01); *G01J 3/0237* (2013.01); *G01J 3/4412* (2013.01); *G01N 21/65* (2013.01)

(58) Field of Classification Search
CPC ............ G01J 3/027; G01J 3/0278; G01J 3/44; G01N 2021/656; G01N 21/55; G01N 21/00; A61B 5/0075
See application file for complete search history.

(56) References Cited

U.S. PATENT DOCUMENTS

| | | |
|---|---|---|
| 6,998,247 B2 | 2/2006 | Monfre et al. |
| 7,672,702 B2 | 3/2010 | Hwang et al. |

(Continued)

FOREIGN PATENT DOCUMENTS

| | | |
|---|---|---|
| JP | 2000-314703 A | 11/2000 |
| KR | 10-1855616 B1 | 5/2018 |

(Continued)

OTHER PUBLICATIONS

Ronald Tabaksblat et al. "Confocal Raman Microspectroscopy: Theory and Application to Thin Polymer Samples" Applied Spectroscopy, vol. 46, No.=. 1, 1992, (10 pages total).

*Primary Examiner* — Abdullahi Nur

(74) *Attorney, Agent, or Firm* — Sughrue Mion, PLLC

(57) ABSTRACT

An apparatus for measuring a Raman spectrum may include a processor configured to adjust a Raman probe parameter, set a Raman probe with the Raman probe parameter, obtain a first Raman spectrum of the sample at a first time point and a second Raman spectrum of the sample at a second time point, obtain a difference spectrum between the first Raman spectrum and the second Raman spectrum, determine a degree of similarity between the difference spectrum and an analyte Raman spectrum, determine an optimal Raman probe parameter based on the degree of similarity, and obtain a Raman spectrum of the sample for measuring bio-information by setting the Raman probe with the optimal Raman probe parameter.

17 Claims, 5 Drawing Sheets

(56) References Cited

U.S. PATENT DOCUMENTS

| | | |
|---|---|---|
| 9,538,943 B1 | 1/2017 | Cross et al. |
| 9,689,743 B2 | 6/2017 | Liu et al. |
| 2004/0012777 A1 | 1/2004 | Vijayakumar |
| 2009/0021724 A1* | 1/2009 | Mahadevan-Jansen ............... A61B 5/0075 356/73 |
| 2016/0287154 A1 | 10/2016 | Chong |
| 2016/0313546 A1 | 10/2016 | Feldman |
| 2017/0273564 A1 | 9/2017 | Banke |
| 2018/0031482 A1 | 2/2018 | Jagiella et al. |
| 2019/0015023 A1 | 1/2019 | Monfre |

FOREIGN PATENT DOCUMENTS

| | | |
|---|---|---|
| WO | 2014053520 A1 | 4/2014 |
| WO | 2016034448 A1 | 3/2016 |

* cited by examiner

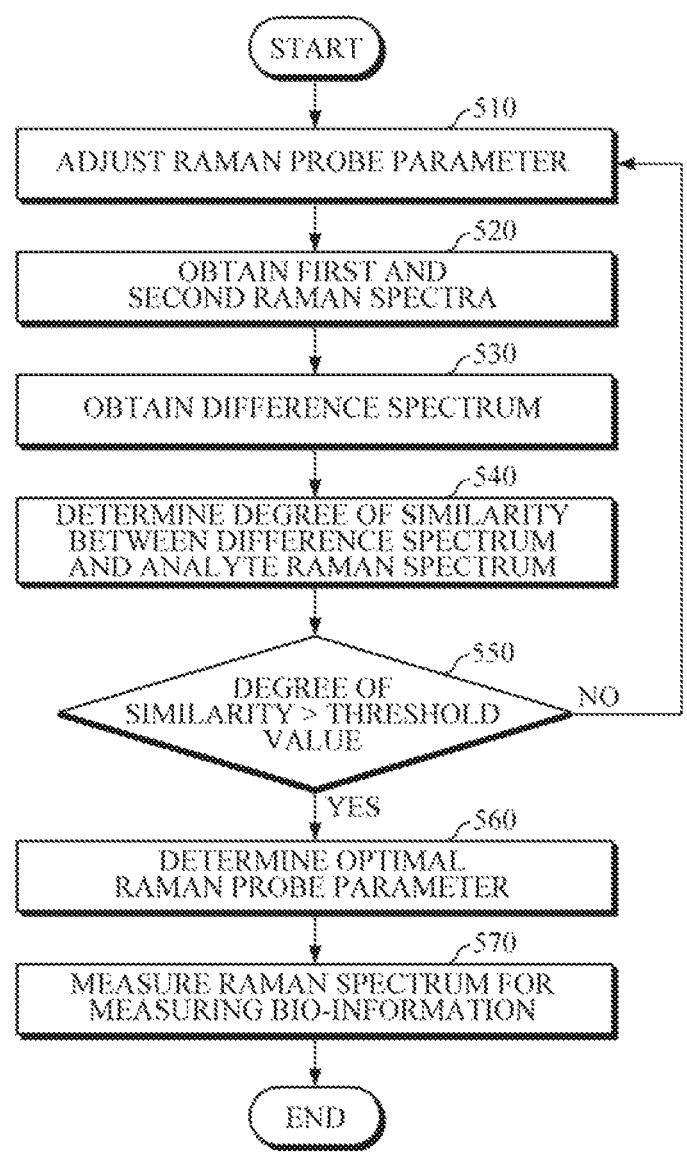

APPARATUS AND METHOD FOR MEASURING RAMAN SPECTRUM

CROSS-REFERENCE TO RELATED APPLICATION(S)

This application is based on and claims priority under 35 U.S.C. § 119 to Korean Patent Application No. 10-2019-0072236, filed on Jun. 18, 2019, in the Korean Intellectual Property Office, the disclosure of which is incorporated by reference herein in its entirety.

BACKGROUND

1. Field

The disclosure relates to Raman spectrum measurement technology.

2. Description of Related Art

Non-invasive glucose sensors, using spectroscopic analytic techniques, such as Raman spectroscopy, may improve convenience of diabetic patients who need to draw blood regularly, or people at risk of metabolic diseases. Particularly, such non-invasive analytic techniques may be used to predict a signal of a blood component by analyzing interstitial fluid present in a dermal layer based on each individual skin spectrum. However, an obtained skin spectrum is mixed with signals of biomolecules (e.g., lipids, proteins, and the like) that pass through an incident light path (e.g., dead skin cells, an epidermal layer, a dermal layer, and the like), such that the obtained skin Raman spectrum has greater background noise compared to a signal of a target material (e.g., glucose).

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Additional aspects will be set forth in part in the description which follows and, in part, will be apparent from the description, or may be learned by practice of the presented embodiments.

The disclosure relates to an apparatus and method for measuring a Raman spectrum.

According to an aspect of the disclosure, an apparatus for measuring a Raman spectrum may include a processor that may adjust a Raman probe parameter, set a Raman probe with the Raman probe parameter, obtain a first Raman spectrum of the sample at a first time point and a second Raman spectrum of the sample at a second time point, obtain a difference spectrum between the first Raman spectrum and the second Raman spectrum, determine a degree of similarity between the difference spectrum and an analyte Raman spectrum, determine an optimal Raman probe parameter based on the degree of similarity, and obtain a Raman spectrum of the sample for measuring bio-information by setting the Raman probe with the optimal Raman probe parameter.

The processor may determine that the Raman probe parameter that maximizes the degree of similarity is the optimal Raman probe parameter by iteratively repeating operations of adjusting the Raman probe parameter, obtaining the first Raman spectrum and the second Raman spectrum, obtaining the difference spectrum, and determining the degree of similarity.

The processor may determine that the Raman probe parameter is the optimal Raman probe parameter based on determining that the degree of similarity exceeds a predetermined threshold value.

In response to determining that the degree of similarity is less than or equal to the predetermined threshold value, the processor may repeat operations of adjusting the Raman probe parameter, obtaining the first Raman spectrum and the second Raman spectrum, obtaining the difference spectrum, and determining the degree of similarity until the degree of similarity between the difference spectrum and the analyte Raman spectrum exceeds the predetermined threshold value.

The Raman probe parameter may include at least one of a spacing between a light collector of the Raman probe and a sample, and a focal depth of the light collector.

The analyte Raman spectrum may be a Raman spectrum of glucose solution.

The processor may determine the degree of similarity using at least one of Euclidean distance, Manhattan Distance, cosine distance, Mahalanobis Distance, Jaccard coefficient, extended Jaccard coefficient, Pearson's correlation coefficient, and Spearman's correlation coefficient.

The bio-information may be a concentration of analyte, and the analyte includes at least one of glucose, triglycerides, urea, uric acids, lactate, proteins, cholesterol, antioxidants, and ethanol.

The apparatus may include the Raman probe, and the Raman probe may include a light source that may emit light to a sample, a light collector that may collect Raman scattered light from the sample, a spectrometer that may divide the Raman scattered light collected in the light collector based on wavelength, and a photodetector that may receive the Raman scattered light divided based on wavelength.

A method of measuring a Raman spectrum may include adjusting a Raman probe parameter; setting a Raman probe with the Raman probe parameter; obtaining a first Raman spectrum of a sample at a first time point and a second Raman spectrum of the sample at a second time point; obtaining a difference spectrum between the first Raman spectrum and the second Raman spectrum; determining a degree of similarity between the difference spectrum and an analyte Raman spectrum; determining an optimal Raman probe parameter based on the degree of similarity; and obtaining a Raman spectrum of the sample for measuring bio-information by setting the Raman probe with the optimal Raman probe parameter.

The determining of the optimal Raman probe parameter may include determining that the Raman probe parameter that maximizes the degree of similarity is the optimal Raman probe parameter by iteratively repeating the operations of adjusting the Raman probe parameter, obtaining the first Raman spectrum and the second Raman spectrum, obtaining the difference spectrum, and determining the degree of similarity.

The determining of the optimal Raman probe parameter may include determining that the Raman probe parameter is the optimal Raman probe parameter based on determining that the degree of similarity exceeds a predetermined threshold value.

In response to determining that the degree of similarity is less than or equal to the threshold value, the determining of the optimal Raman probe parameter may include iteratively repeating the operations of adjusting the Raman probe parameter, obtaining the first Raman spectrum and the second Raman spectrum, obtaining the difference spectrum, and determining the degree of similarity until the degree of similarity between the difference spectrum and the analyte Raman spectrum exceeds the predetermined threshold value.

The Raman probe parameter may include at least one of a spacing between a light collector of the Raman probe and the sample, and a focal depth of the light collector.

The analyte Raman spectrum may be a Raman spectrum of glucose solution.

The determining of the degree of similarity may include determining the degree of similarity using at least one of Euclidean distance, Manhattan Distance, cosine distance, Mahalanobis Distance, Jaccard coefficient, extended Jaccard coefficient, Pearson's correlation coefficient, and Spearman's correlation coefficient.

The bio-information may be a concentration of an analyte, and the analyte includes at least one of glucose, triglycerides, urea, uric acids, lactate, proteins, cholesterol, antioxidants, and ethanol.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 5 is a flowchart illustrating a method of measuring a Raman spectrum according to an embodiment.

Figure 1:
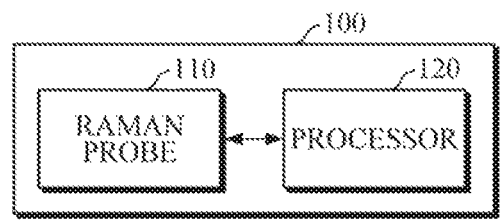
FIG. 1 is a diagram illustrating an apparatus for measuring a Raman spectrum according to an embodiment.

Throughout the drawings and the detailed description, unless otherwise described, the same drawing reference numerals may refer to the same elements, features, and structures. The relative size and depiction of these elements, features, and structures may be exaggerated for clarity, illustration, and convenience.

DETAILED DESCRIPTION

Hereinafter, example embodiments of the present disclosure will be described in detail with reference to the accompanying drawings. It should be noted that, in the drawings, the same reference symbols may refer to the same parts although illustrated in other drawings. In the following description, a detailed description of known functions and configurations incorporated herein may be omitted so as to not obscure the subject matter of the present disclosure.

Process steps described herein may be performed differently from a specified order, unless a specified order is clearly stated in the context of the disclosure. That is, each step may be performed in a specified order, substantially at the same time, in a reverse order, or in any other order.

Further, the terms used throughout this specification are defined in consideration of the functions according to exemplary embodiments, and can be varied according to a purpose of a user or manager, precedent, and so on. Therefore, definitions of the terms should be made on the basis of the overall context.

It should be understood that, although the terms "first," "second," etc. may be used herein to describe various elements, these elements should not be limited by these terms. These terms do not necessarily imply order, preference, or precedence, and might only be used to distinguish one element from another. Any references to the singular form of a term may include the plural form of the term unless expressly stated otherwise in the present specification. It should be understood that terms such as "including," "having," etc., are intended to indicate the existence of the features, numbers, steps, actions, components, parts, or combinations thereof, disclosed in the specification, and are not intended to preclude the possibility that one or more other features, numbers, steps, actions components, parts, or combinations thereof, may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented as hardware (e.g., a circuit, a microchip, a processor, etc.), software (e.g., instructions, code, a program, an application, firmware, etc.), or a combination of both.

Figure 2:
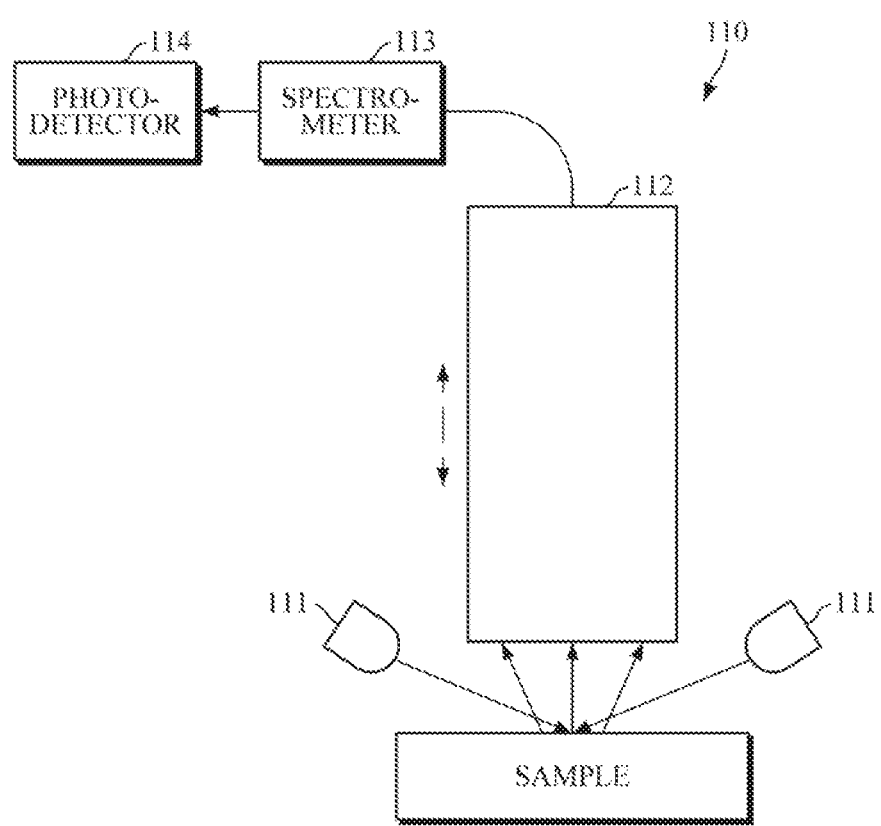
FIG. 2 is a diagram illustrating a Raman probe shown in FIG. 1 according to an embodiment.

FIG. 1 is a diagram illustrating an apparatus for measuring a Raman spectrum according to an embodiment, and FIG. 2 is a diagram illustrating a Raman probe 110 shown in FIG. 1 according to an embodiment.

Referring to FIG. 1, the apparatus 100 for measuring a Raman spectrum may include a Raman probe 110 and a processor 120.

The Raman probe 110 may emit light to a sample, and collect Raman scattered light from the sample. As shown in FIG. 2, the Raman probe 110 may include a light source 111, a light collector 112, a spectrometer 113, and a photodetector 114.

The light source 111 may emit light to the sample. To this end, the light source 111 may include a single light source 111 or a plurality of light sources 111. For example, the light source 111 may emit light of a predetermined wavelength, for example, visible light or infrared light, to the sample. However, the embodiment is not limited thereto, such that the wavelength of light to be emitted from the light source may be changed according to the measurement purpose or an analyte. Each of the light sources 111 may be configured as a single light emitter, or may be configured as a set of a plurality of light emitters. Where each of the light sources 111 is configured as a set of a plurality of light emitters, the plurality of light emitters may emit light of different wavelengths or light of the same wavelength to suit the measurement purpose. According to one embodiment, the light source 111 may be configured as a light emitting diode (LED) or a laser diode, but is not limited thereto.

According to one embodiment, the light source 111 may further include a filter (e.g., a cleanup filter, a bandpass filter, and the like) for selecting light of a specific wavelength and/or an optical element (e.g., a reflection mirror or the like) which allows the emitted light to be directed to a desired position.

According to one embodiment, the light source 111 may be implemented such that the sample is obliquely irradiated from a side of the light collector 112. However, the embodiment may not be limited thereto and the light source 111 may be implemented to emit light in a direction perpendicular to the sample. That is, the position of the light source 111 and an incident angle of light with respect to the sample are not particularly limited.

According to one embodiment, the light source 111 may be fixed at a specific position and all or some of the elements of the light source 111 may be implemented to move or rotate up and down, left and right, or back and forth.

The light collector 112 may collect Raman scattered light from the sample. According to one embodiment, the light collector 112 may include a filter (e.g., a long pass filter, a clean-up filter, or the like), a lens (e.g., a collection lens, a collimating lens, a focusing lens, or the like), a fiber, a waveguide, a grating, and the like.

According to one embodiment, the light collector 112 may be configured to be movable up and down in a direction perpendicular to the sample such that spacing between the light collector 112 and the sample can be adjusted, or may be configured to enable a focal depth of the light collector 112 to be adjusted.

The spectrometer 113 may spatially divide the Raman scattered light collected by the light collector 112 by wavelength. According to one embodiment, the spectrometer 113 may include a prism, a grating, or the like.

The photodetector 114 may receive the Raman scattered light divided by wavelength in the spectrometer 113. According to one embodiment, the photodetector 114 may include a photodiode, a photo transistor, an image sensor (e.g., a charge-coupled device (CCD) image sensor, a complementary metal-oxide semiconductor (CMOS) image sensor, or the like), and the like. The photodetector 114 may be configured as one device or may be configured as an array of a plurality of devices.

The processor 120 may control an overall operation of the apparatus 100 for measuring a Raman spectrum and process various signals related to the operation of the apparatus 100 for measuring a Raman spectrum.

The processor 120 may acquire a Raman spectrum of the sample on the basis of the Raman scattered light received from the photodetector 114.

The processor 120 may determine an optimal probe parameter for estimating bio-information by controlling the Raman probe 110 periodically or each time a predetermined event occurs, and may acquire the optimal Raman spectrum for estimating bio-information by setting the Raman probe 110 with the determined Raman probe parameter. In this case, the Raman probe parameter may include spacing between the light collector 112 and the sample and a focal depth of the light collector 112, but is not limited thereto. In addition, the bio-information may be the concentration of an in-vivo analyte, and the analyte may include glucose, triglycerides, urea, uric acids, lactate, proteins, cholesterol, antioxidants (e.g., vitamins, carotenoids, flavonoids, ascorbic acids, tocopherols, and the like), ethanol, and the like, but is not limited thereto. Where the in-vivo analyte is glucose, the bio-information may be blood glucose, and hereinafter, a case where the bio-information is blood glucose will be described for convenience of description.

According to one embodiment, the processor 120 may acquire a Raman spectrum (hereinafter, referred to as a "first Raman spectrum") of the sample for each Raman probe parameter at a first time point and a Raman spectrum (hereinafter, referred to as a "second Raman spectrum") of the sample at a second time point after a predetermined time period from the first time point by adjusting the Raman probe parameters. Also, the processor 120 may obtain a difference spectrum between the first Raman spectrum and the second Raman spectrum for each Raman probe parameter, and determine the optimal Raman probe parameter for estimating bio-information on the basis of a degree of similarity between the obtained difference spectrum and an analyte Raman spectrum. In this case, the analyte Raman spectrum may be a Raman spectrum of an analyte solution, and may be a Raman spectrum of a glucose solution when the analyte is glucose. The processor 120 may use various similarity algorithms, such as Euclidean distance, Manhattan Distance, cosine distance, Mahalanobis Distance, Jaccard coefficient, extended Jaccard coefficient, Pearson's correlation coefficient, Spearman's correlation coefficient, and the like.

For example, the processor 120 may adjust the Raman probe parameter and set the Raman probe 110 with the adjusted Raman probe parameter. The processor 120 may obtain the first Raman spectrum and the second Raman spectrum of the sample using the set Raman probe 110, and obtain the difference spectrum by subtracting the second Raman spectrum from the first Raman spectrum, or subtracting the first Raman spectrum from the first Raman spectrum. In addition, the processor may determine a degree of similarity between the difference spectrum and the analyte Raman spectrum (e.g., a Raman spectrum of glucose solution) using the above-described various similarity algorithms. The processor 120 may repeat operations of adjusting the Raman probe parameter, obtaining the first Raman spectrum and the second Raman spectrum, obtaining a difference spectrum, and determining a degree of similarity as many times as predetermined, and may determine that a Raman probe parameter which maximizes the degree of similarity between the difference spectrum and the analyte Raman spectrum is the optimal Raman probe parameter.

In another example, the processor 120 may adjust the Raman probe parameter, and set the Raman probe 110 with the adjusted Raman probe parameter. The processor 120 may obtain the first Raman spectrum and the second Raman spectrum of the sample using the set Raman probe 110, and obtain a difference spectrum by subtracting the second Raman spectrum from the first Raman spectrum or subtracting the first Raman spectrum from the second Raman spectrum. Also, the processor 120 may determine a degree of similarity between the difference spectrum and an analyte Raman spectrum (e.g., a Raman spectrum of glucose solution) using the above-described various similarity algorithms, and determine the Raman probe parameter that causes the determined degree of similarity to exceed a predetermined threshold value as an optimal Raman probe parameter. In addition, based on determining that the degree of similarity between the difference spectrum and the analyte Raman spectrum is less than or equal to the threshold value, the processor 120 may repeat the operations of adjusting the Raman probe parameter, obtaining the first Raman spectrum and the second Raman spectrum, obtaining a difference spectrum, and determining the degree of similarity until the degree of similarity between the difference spectrum and the analyte Raman spectrum exceeds the predetermined threshold value.

The processor 120 may set the Raman probe 110 with the determined optimal Raman probe parameter, obtain an optimal Raman spectrum for estimating bio-information using the set Raman probe 110, and estimate bio-information by analyzing the obtained optimal Raman spectrum.

According to one embodiment, the apparatus 100 for measuring a Raman spectrum sets the Raman probe 110 by determining the optimal Raman probe parameter periodically or each time a predetermined event occurs, so that a Raman spectrum with a high signal-to-noise ratio (SNR) can be obtained, thereby improving accuracy of bio-information estimation.

Figure 3:
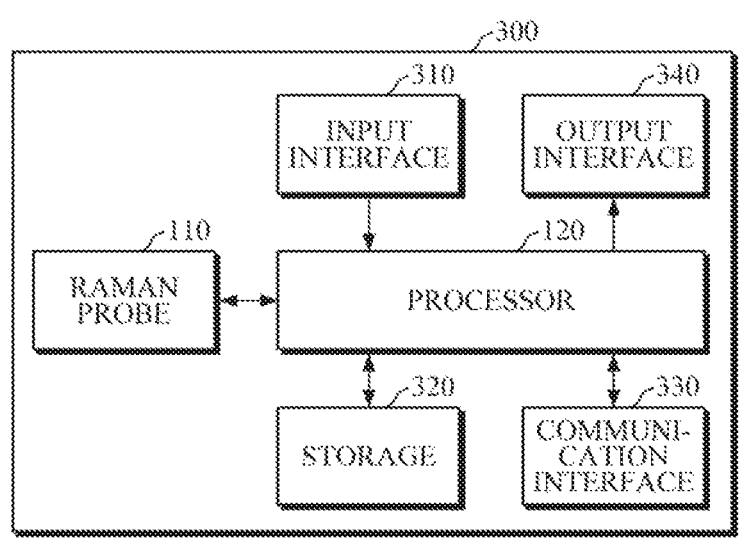
FIG. 3 is a diagram illustrating an apparatus for measuring a Raman spectrum according to an embodiment.

FIG. 3 is a diagram illustrating an apparatus for measuring a Raman spectrum according to an embodiment.

Referring to FIG. 3, an apparatus 300 for measuring a Raman spectrum may include a Raman probe 110, a processor 120, an input interface 310, a storage 320, a communication interface 330, and an output interface 340. Here, the Raman probe 110 and the processor 120 are substantially the same or similar to those described with reference to FIGS. 1 and 2, and hence detailed descriptions thereof will not be reiterated.

The input interface 310 may receive various operation signals from a user based on a user input. According to one embodiment, the input interface 310 may include a keypad, a dome switch, a touchpad, a jog wheel, a jog switch, a hardware button, and the like. Particularly, when a touchpad has a layered structure with a display, this structure may be referred to as a touch screen.

Programs or commands for operation of the apparatus 300 for measuring a Raman spectrum may be stored in the storage 320, and data input to the apparatus 300 and data processed in the apparatus 300 may be stored therein.

The storage 320 may include at least one type of storage medium, such as a flash memory type, a hard disk type, a multimedia card micro type, a card type memory (e.g., secure digital (SD) or extreme digital (XD) memory), random access memory (RAM), static random access memory (SRAM), read-only memory (ROM), electrically erasable programmable read-only memory (EEPROM), programmable read-only memory (PROM), a magnetic memory, a magnetic disk, and an optical disk. In addition, the apparatus 300 for measuring a Raman spectrum may operate an external storage medium, such as a web storage that performs the storage function of the storage 320 on the Internet.

The communication interface 330 may communicate with an external device. For example, the communication interface 330 may transmit the input data, the stored data, the processed data, and the like, of the apparatus 300 for measuring a Raman spectrum to the external device, and receive a variety of data to obtain a Raman spectrum and/or estimate bio-information from the external device.

In this case, the external device may be medical equipment using the input data, the stored data, the processed data, and the like, of the apparatus 300 for measuring a Raman spectrum, a printer to print out results, or a display device to display the results. In addition, the external device may be a digital television (TV), a desktop computer, a mobile phone, a smartphone, a tablet computer, a notebook computer, a personal digital assistant (PDA), a portable multimedia player (PMP), a navigation device, an MP3 player, a digital camera, a wearable device, or the like, but is not limited thereto.

The communication interface 330 may communicate with the external device using Bluetooth communication, Bluetooth low energy (BLE) communication, near field communication (NFC), wireless local area network (WLAN) communication, ZigBee communication, infrared data association (IrDA) communication, wireless fidelity (Wi-Fi) direct (WFD) communication, ultra-wideband (UWB) communication, Ant+ communication, Wi-Fi communication, radio frequency identification (RFID) communication, third generation (3G) communication, fourth generation (4G) communication, fifth generation (5G) communication, or the like. However, these are merely examples, and the embodiment is not limited thereto.

The output interface 340 may output the input data, the stored data, the processed data, and the like, of the apparatus 300 for measuring a Raman spectrum. According to one embodiment, the output interface 340 may output the input data, the stored data, the processed data, and the like, of the apparatus 300 using at least one of an acoustic method, a visual method, and a tactile method. To this end, the output interface 340 may include a display, a speaker, a vibrator, and the like.

Figure 4:
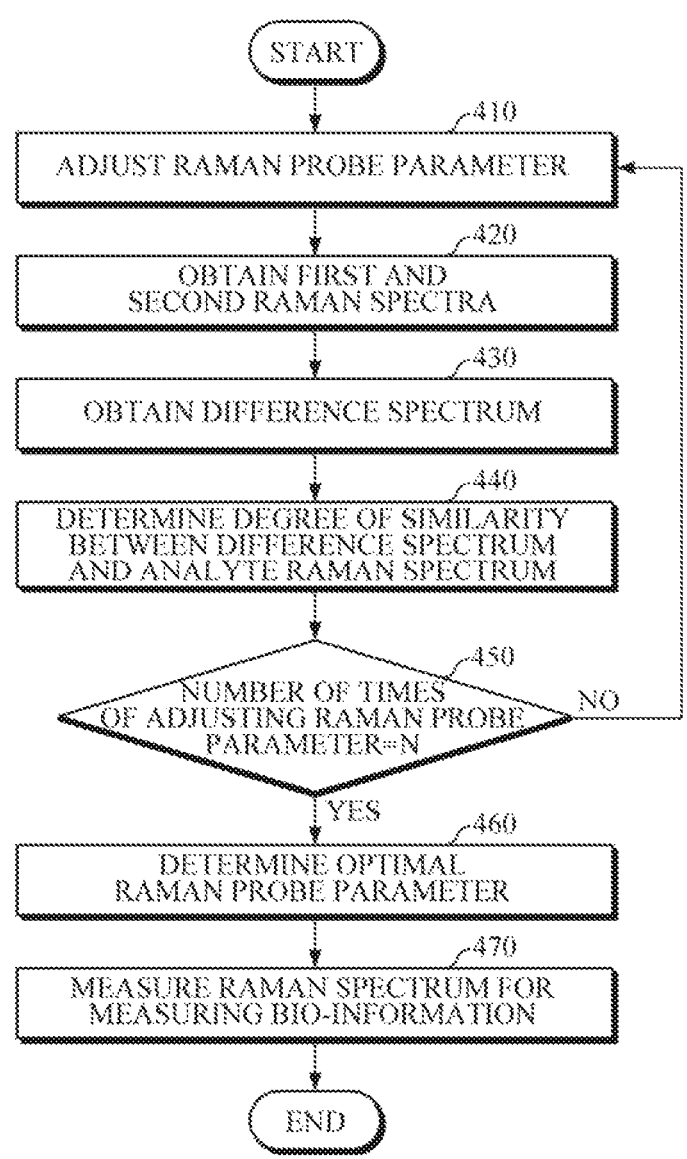
FIG. 4 is a flowchart illustrating a method of measuring a Raman spectrum according to an embodiment.

FIG. 4 is a flowchart illustrating a method of measuring a Raman spectrum according to an embodiment. The method of FIG. 4 may be performed by the apparatuses 100 or 300 for measuring a Raman spectrum shown in FIG. 1 or 3.

Referring to FIG. 4, the apparatus for measuring a Raman spectrum may adjust a Raman probe parameter (operation 410). In this case, the Raman probe parameter may include a spacing between the light collector of the Raman probe and a sample, a focal depth of the light collector of the Raman probe, and the like.

The apparatus for measuring a Raman spectrum may set the Raman probe with the Raman probe parameter, and obtain a first Raman spectrum of the sample at a first time point and a second Raman spectrum of the sample at a second time point by using the set Raman probe (operation 420). In this case, the second time point may be a time point after a predetermined time period from the first time point.

The apparatus for measuring a Raman spectrum may obtain a difference spectrum between the first Raman spectrum and the second Raman spectrum (operation 430). For example, the apparatus for measuring a Raman spectrum may obtain the difference spectrum by subtracting the second Raman spectrum from the first Raman spectrum or subtracting the first Raman spectrum from the second Raman spectrum. By doing so, the apparatus for measuring a Raman spectrum may eliminate, or reduce, effects caused by factors other than an analyte.

The apparatus for measuring a Raman spectrum may determine a degree of similarity between the difference spectrum and an analyte Raman spectrum (e.g., a Raman spectrum of glucose solution) (operation 440). According to one embodiment, the apparatus for measuring a Raman spectrum may determine the degree of similarity between the difference spectrum and the analyte Raman spectrum using various similarity algorithms, such as Euclidean distance, Manhattan Distance, cosine distance, Mahalanobis Distance, Jaccard coefficient, extended Jaccard coefficient, Pearson's correlation coefficient, Spearman's correlation coefficient, and the like.

The apparatus for measuring a Raman spectrum may determine whether or not the number of times of adjusting the Raman probe parameter reaches a predetermined number (n) of times (operation 450), and may iteratively repeat the operations of repeating the Raman probe parameter (operation 410), obtaining the first Raman spectrum and the second Raman spectrum (operation 420), and determining the degree of similarity (operation 440) based on determining that the number of times of adjusting the Raman probe parameter is less than the predetermined number (n) of times (operation 450—NO).

Based on determining that the number of times of adjusting the Raman probe parameter is greater than or equal to the predetermined number (n) of times (operation 450—YES), the apparatus for measuring a Raman spectrum may determine that a Raman probe parameter that maximizes the degree of similarity between the difference spectrum and the analyte Raman spectrum is an optimal Raman probe parameter (operation 460).

The apparatus for measuring a Raman spectrum may set the Raman probe with the determined optimal Raman probe parameter, and obtain a Raman spectrum of the sample for estimating bio-information by using the set Raman probe (operation 470).

According to an additional embodiment, based on the Raman spectrum of the sample for estimating bio-information being acquired, the apparatus for measuring a Raman spectrum may estimate bio-information of the sample by analyzing the acquired Raman spectrum. In this case, the bio-information may use various similarity algorithms, such as Euclidean distance, Manhattan Distance, cosine distance, Mahalanobis Distance, Jaccard coefficient, extended Jaccard coefficient, Pearson's correlation coefficient, Spearman's correlation coefficient, and the like.

FIG. 5 is a flowchart illustrating a method of measuring a Raman spectrum according to an embodiment. The method of FIG. 5 may be performed by the apparatuses 100 or 300 for measuring a Raman spectrum shown in FIG. 1 or 3.

Referring to FIG. 5, the apparatus for measuring a Raman spectrum may adjust a Raman probe parameter (operation 510). In this case, the Raman probe parameter may include a spacing between the light collector of the Raman probe and a sample, a focal depth of the light collector of the Raman probe, and the like.

The apparatus for measuring a Raman spectrum may set Raman probe with the adjusted Raman probe parameter, and obtain a first Raman spectrum of the sample at a first time point and a second Raman spectrum of the sample at a second time point using the set Raman probe (operation 520). In this case, the second time point may be a time point after a predetermined time period from the first time point.

The apparatus for measuring a Raman spectrum may obtain a difference spectrum between the first Raman spectrum and the second Raman spectrum (operation 530). For example, the apparatus for measuring a Raman spectrum may obtain the difference spectrum by subtracting the second Raman spectrum from the first Raman spectrum or subtracting the first Raman spectrum from the second Raman spectrum. In so doing, the apparatus for measuring a Raman spectrum may eliminate, or reduce, effects caused by factors other than an analyte.

The apparatus for measuring a Raman spectrum may determine a degree of similarity between the difference spectrum and an analyte Raman spectrum (e.g., a Raman spectrum of glucose solution) (operation 540). According to one embodiment, the apparatus for measuring a Raman spectrum may determine the degree of similarity between the difference spectrum and the analyte Raman spectrum using various similarity algorithms, such as Euclidean distance, Manhattan Distance, cosine distance, Mahalanobis Distance, Jaccard coefficient, extended Jaccard coefficient, Pearson's correlation coefficient, Spearman's correlation coefficient, and the like.

The apparatus for measuring a Raman spectrum may determine whether or not the degree of similarity between the difference spectrum and the analyte Raman spectrum exceeds a predetermined threshold value (operation 550), and determine that a Raman probe parameter that causes the degree of similarity between the difference spectrum and the analyte Raman spectrum to exceed the predetermined threshold value is an optimal probe parameter (operation 560).

The apparatus for measuring a Raman spectrum may set a Raman probe with the determined optimal Raman probe parameter, and obtain a Raman spectrum of the sample for measuring bio-information using the set Raman probe (operation 570).

Based on determining that the degree of similarity between the difference spectrum and the analyte Raman spectrum is less than or equal to the predetermined threshold value, the apparatus for measuring a Raman spectrum may iteratively repeat the operations of adjusting the Raman probe parameter (operation 510), obtaining the first Raman spectrum and the second Raman spectrum (operation 520), obtaining the difference spectrum (530), and determining the degree of similarity (operation 540) until the degree of similarity between the difference spectrum and the analyte Raman spectrum exceeds the predetermined threshold value.

Also, according to an additional embodiment, the apparatus for measuring a Raman spectrum may estimate bio-information of the sample by analyzing the obtained Raman spectrum based on the Raman spectrum of the sample for measuring bio-information being obtained.

The current embodiments can be implemented as computer readable code stored in a non-transitory computer readable medium. Code and code segments constituting the computer program can be inferred by a skilled computer programmer in the art. The computer readable medium includes all types of recording media in which computer readable data are stored. Examples of the computer readable medium include a ROM, a RAM, a CD-ROM, a magnetic tape, a floppy disk, and an optical data storage. Further, the computer readable medium may be implemented in the form of a carrier wave such as Internet transmission. In addition, the computer readable medium may be distributed to computer systems over a network, in which computer readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for measuring a Raman spectrum, the apparatus comprising:
    a processor configured to:
        adjust a Raman probe parameter;
        set a Raman probe with the Raman probe parameter;
        obtain a first Raman spectrum of the sample at a first time point and a second Raman spectrum of the sample at a second time point;
        obtain a difference spectrum between the first Raman spectrum and the second Raman spectrum;
        determine a degree of similarity between the difference spectrum and an analyte Raman spectrum;
        determine an optimal Raman probe parameter based on the degree of similarity; and
        obtain a Raman spectrum of the sample for measuring bio-information by setting the Raman probe with the optimal Raman probe parameter.

2. The apparatus of claim 1, wherein the processor is configured to determine that the Raman probe parameter that maximizes the degree of similarity is the optimal Raman probe parameter by iteratively repeating operations of adjusting the Raman probe parameter, obtaining the first Raman spectrum and the second Raman spectrum, obtaining the difference spectrum, and determining the degree of similarity.

3. The apparatus of claim 1, wherein the processor is configured to determine that the Raman probe parameter is the optimal Raman probe parameter based on determining that the degree of similarity exceeds a predetermined threshold value.

4. The apparatus of claim 3, wherein in response to determining that the degree of similarity is less than or equal to the predetermined threshold value, the processor is configured to repeat operations of adjusting the Raman probe parameter, obtaining the first Raman spectrum and the second Raman spectrum, obtaining the difference spectrum, and determining the degree of similarity until the degree of similarity between the difference spectrum and the analyte Raman spectrum exceeds the predetermined threshold value.

5. The apparatus of claim 1, wherein the Raman probe parameter includes at least one of a spacing between a light collector of the Raman probe and a sample, and a focal depth of the light collector.

6. The apparatus of claim 1, wherein the analyte Raman spectrum is a Raman spectrum of glucose solution.

7. The apparatus of claim 1, wherein the processor is configured to determine the degree of similarity using at least one of Euclidean distance, Manhattan Distance, cosine distance, Mahalanobis Distance, Jaccard coefficient, extended Jaccard coefficient, Pearson's correlation coefficient, and Spearman's correlation coefficient.

8. The apparatus of claim 1, wherein the bio-information is a concentration of analyte, and the analyte includes at least one of glucose, triglycerides, urea, uric acids, lactate, proteins, cholesterol, antioxidants, and ethanol.

9. The apparatus of claim 1, wherein the apparatus further comprises the Raman probe comprising:
   a light source configured to emit light to a sample;
   a light collector configured to collect Raman scattered light from the sample;
   a spectrometer configured to divide the Raman scattered light collected in the light collector based on wavelength; and
   a photodetector configured to receive the Raman scattered light divided based on wavelength.

10. A method of measuring a Raman spectrum, the method comprising:
    adjusting a Raman probe parameter;
    setting a Raman probe with the Raman probe parameter;
    obtaining a first Raman spectrum of a sample at a first time point and a second Raman spectrum of the sample at a second time point;
    obtaining a difference spectrum between the first Raman spectrum and the second Raman spectrum;
    determining a degree of similarity between the difference spectrum and an analyte Raman spectrum;
    determining an optimal Raman probe parameter based on the degree of similarity; and
    obtaining a Raman spectrum of the sample for measuring bio-information by setting the Raman probe with the optimal Raman probe parameter.

11. The method of claim 10, wherein the determining of the optimal Raman probe parameter comprises determining that the Raman probe parameter that maximizes the degree of similarity is the optimal Raman probe parameter by iteratively repeating the operations of adjusting the Raman probe parameter, obtaining the first Raman spectrum and the second Raman spectrum, obtaining the difference spectrum, and determining the degree of similarity.

12. The method of claim 10, wherein the determining of the optimal Raman probe parameter comprises determining that the Raman probe parameter is the optimal Raman probe parameter based on determining that the degree of similarity exceeds a predetermined threshold value.

13. The method of claim 12, wherein in response to determining that the degree of similarity is less than or equal to the threshold value, the determining of the optimal Raman probe parameter comprises iteratively repeating the operations of adjusting the Raman probe parameter, obtaining the first Raman spectrum and the second Raman spectrum, obtaining the difference spectrum, and determining the degree of similarity until the degree of similarity between the difference spectrum and the analyte Raman spectrum exceeds the predetermined threshold value.

14. The method of claim 10, wherein the Raman probe parameter includes at least one of a spacing between a light collector of the Raman probe and the sample, and a focal depth of the light collector.

15. The method of claim 10, wherein the analyte Raman spectrum is a Raman spectrum of glucose solution.

16. The method of claim 10, wherein the determining of the degree of similarity comprises determining the degree of similarity using at least one of Euclidean distance, Manhattan Distance, cosine distance, Mahalanobis Distance, Jaccard coefficient, extended Jaccard coefficient, Pearson's correlation coefficient, and Spearman's correlation coefficient.

17. The method of claim 10, wherein the bio-information is a concentration of an analyte, and the analyte includes at least one of glucose, triglycerides, urea, uric acids, lactate, proteins, cholesterol, antioxidants, and ethanol.

* * * * *